United States Patent
Saunders et al.

(10) Patent No.: US 7,024,010 B2
(45) Date of Patent: Apr. 4, 2006

(54) ELECTRONIC EARPLUG FOR MONITORING AND REDUCING WIDEBAND NOISE AT THE TYMPANIC MEMBRANE

(75) Inventors: William R. Saunders, Blacksburg, VA (US); Michael A. Vaudrey, Blacksburg, VA (US); Andre Goldstein, Blacksburg, VA (US)

(73) Assignee: Adaptive Technologies, Inc., Blacksburg, VA (US)

( * ) Notice: Subject to any disclaimer, the term of this patent is extended or adjusted under 35 U.S.C. 154(b) by 386 days.

(21) Appl. No.: 10/440,619

(22) Filed: May 19, 2003

(65) Prior Publication Data

US 2004/0234094 A1 Nov. 25, 2004

(51) Int. Cl.
*H04R 25/00* (2006.01)

(52) U.S. Cl. .................... 381/317; 381/71.6
(58) Field of Classification Search ............ 381/71.2, 381/71.1, 71.6, 71.7, 72, 73.1, 94.1, 94.9, 381/23.1, 317, 327, 380, 312, 318, 320, 321, 381/71.8, 71.13, 71.14
See application file for complete search history.

(56) References Cited

U.S. PATENT DOCUMENTS

| | | | |
|---|---|---|---|
| 4,985,925 A | 1/1991 | Langberg et al. | |
| 5,305,387 A | 4/1994 | Sapiejewski | |
| 5,631,965 A | 5/1997 | Chang et al. | |
| 5,740,258 A | 4/1998 | Goodwin-Johansson | |
| 6,661,901 B1 * | 12/2003 | Svean et al. | 381/328 |
| 6,683,965 B1 * | 1/2004 | Sapiejewski | 381/380 |
| 6,728,385 B1 * | 4/2004 | Kvaløy et al. | 381/328 |

OTHER PUBLICATIONS

K. Buck, et al. "An Active Noise reduction Ear Plug with Driven Feedback Loop.".

Phillipe Herzog, "Electroacoustic Design of An Active Earplug".

Thomas R. Harley, "Digital Active Noise reduction Ear Plugs".

* cited by examiner

*Primary Examiner*—Sinh Tran
*Assistant Examiner*—Brian Ensey
(74) *Attorney, Agent, or Firm*—Roberts Abokhair & Mardula, LLC (57) ABSTRACT

An electronic earplug for wideband control of pressures at the tympanic membrane is presented. A unique methodology of determining effective component placement inside an earplug that provides acoustic isolation between the ambient noise and tympanic membrane is explained. Methods for providing accurate dosimetry and improved active control result from the unique earplug design process, leading to very wideband active noise reduction at the tympanic membrane.

60 Claims, 6 Drawing Sheets

Figure 1: Generic electronic earplug design inserted in ear canal

Figure 3: Open Loop FRF's TM is dashed and microphone is solid, for an accurate earplug design

Figure 4: Simplified closed Loop FRF

Figure 5: Precise closed loop FRF's (TM is dashed, microphone is solid)

Figure 6: Closed loop FRF's (TM is dashed, microphone is solid)

Figure 7: Experimental closed loop FRF's (TM is dashed, microphone is solid)

Figure 8: Prior art earplug design with improved control bandwidth: conventional open loop frfs (solid is microphone, dashed is TM)

Figure 9: Prior art earplug design with improved control bandwidth: conventional closed loop frfs (solid is microphone, dashed is TM)

Figure 10: Open loop frfs (solid is microphone, dashed is TM) for new electronic earplug design Figure 11: Closed loop frfs (solid is microphone, dashed is TM) for new electronic earplug design illustrated performance agreement past 3 kHz.

ELECTRONIC EARPLUG FOR MONITORING AND REDUCING WIDEBAND NOISE AT THE TYMPANIC MEMBRANE

FIELD OF INVENTION

The present invention relates generally to the field of electronic hearing protector devices. More specifically, the present invention relates to an electronic earplug and a method for designing an electronic earplug that accurately monitors sound pressure at the tympanic membrane for a wide range of frequencies and provides active noise reduction (ANR).

BACKGROUND OF THE INVENTION

Active noise reduction (ANR) earplugs have been identified as viable means for suppressing the sound pressure levels inside users' ear canals. The primary advantage of the ANR earplug is its ability to suppress noise inside a smaller occluded space than the corresponding occluded space in prior ANR earmuff designs. This reduction in the volume of the occluded space causes the corresponding reduction in dimension of the acoustic dynamic system to be controlled, thereby allowing control of a broader frequency bandwidth. A significant disadvantage associated with prior ANR earplugs is that all earplug constructions offered thus far cannot guarantee that the electronic control attenuation at an earplug microphone will be the same as the control attenuation at the end of the ear canal, i.e. at the surface of the tympanic membrane.

At issue in ANR earplug design is the need to control sound pressure at the eardrum over a wide frequency band. Prior research and design has focused on controlling the pressure at the earplug (or error) microphone. Prior ANR earplug designs have failed to appreciate the critical differences in reducing sound pressure at the earplug microphone in the control circuit versus reducing sound pressure at the user's tympanic membrane.

A number of ANR earplug designs are described in "An Active Noise reduction Ear Plug with Digitally Driven Feedback Loop," by K. Buck, V. Zimpter and P. Hamery, a paper presented at Inter-Noise 2002, the International Congress and Exposition on Noise control Engineering, Aug. 19–21, 2002 (herein, "Buck"). One such design used a walkman-type loud speaker. According to Buck, the closed-loop performance of that design is not impressive, largely due to the electroacoustic transfer function of the walkman-type loud speaker.

Buck also describes a piezoceramic actuator. A flat-plate type device exhibited an electroacoustic transfer function that was amenable to ANR applications. However, the pressure output of the flat-plate piezoceramic actuator was insufficient for ANR applications, particularly in a noisy environment. A tube-type piezoceramic actuator was also tested and claimed as possible for use inside the ear canal, without specification of any dimensions. Like the flat-plate design, the transfer function of the tube-type piezoceramic actuator was acceptable, but the prototype device was too inefficient in output sound power for commercial applications. Buck concludes that the main obstacle in designing ANR earplugs is related to the transducers [actuators]. Controlling the pressure at the eardrum location not addressed by Buck.

Another paper, "Electroacoustic Design of an Active Earplug," by Phillipe Herzog, a paper presented at Inter-Noise 2002, the International Congress and Exposition on Noise control Engineering, Aug. 19–21, 2002 (herein, "Herzog"), also discusses the design of earplugs with ANR. Herzog also comments on the design constraints posed by current choices for actuators:

The piezoelectric speaker would allow to use a simpler control filter, but still require expensive developments. An cheaper solution, requiring also a simple control filter, would be electret speaker, if a relatively low pressure is to be controlled. Conversely, the emergence efficient numerical control filters may allow us to use existing dynamic speakers. In any case, the maximum pressure inside the ear canal remains a critical criterion.

Buck and Herzog both focus on the actuator as a main obstacle in the design of an effective earplug with ANR system. Both papers fail to address how to design an earplug so that the electronic ANR performance can be compared to, and tailored to match the performance at the tympanic membrane.

A publication by Thomas R. Harley, et al., titled "Digital Active Noise reduction Ear Plugs," Air Force Research Laboratory Report AFRL-HE-WP-TR-2001-0042, points out that ANR earplugs tested in the ear canal simulator of a KEMAR mannequin exhibited discrepancies that showed ". . . cancellation at the earplug microphone did not guarantee cancellation at the (mannequin) eardrum." However, human test subjects were not tested to determine if this discrepancy was also observed for human tympanic membranes. In addition, the paper does not offer any explanations for this discrepancy nor does it provide any solutions to overcome critical differences in performance between the electronic ANR system and ANR performance at the eardrum of a KEMAR mannequin or the tympanic membrane of a human.

In U.S. Pat. No. 4,985,925 issued to Langberg et al. (Langberg) presents the idea of a small electroacoustic actuator used as part of a feedback system to close the loop on a second electroacoustic transducer (microphone) to suppress the sound pressure levels observed by the microphone over a relatively narrow band of frequencies (20 Hz to 1 kHz). The speaker and microphone locations for the earplug embodiments identified in Langberg are defined simply as "in proximity of an ear canal." Figure 2 of Langberg indicates that the speaker is just outside of the ear canal and the microphone is located just inside the ear canal entrance. Langberg discusses the phase of the electroacoustic transfer function as a fundamental obstacle to electronic control performance. However, there is no discussion of the impact of transducer placement on noise reduction performance at the eardrum, or the human perceived performance of the resulting control.

U.S. Pat. No. 5,305,387 issued to Sapiejewski teaches the use of a first electroacoustic transducer (actuator) arranged inside the concha of a user, with a second electroacoustic transducer (microphone) situated inside a front cabinet volume and adjacent to the actuator, and intercoupling of first and second transducers with feedback electronic circuitry to actively reduce the noise intensity inside the concha cavity.

U.S. Pat. No. 5,631,965 issued to Chang discusses the use of a microphone to receive an external acoustic sound signal to be electronically processed in the feedforward sense for creation of a sound signal that travels down a tube extending through the ear piece to the ear canal.

U.S. Pat. No. 5,740,258 issued to Goodwin Johansson also discusses a feedforward active noise suppressor that includes an input transducer used to generate an electrical signal in response to sound pressure waves entering the ear canal, then is processed to generate an inverse noise signal applied to the output transducer. No specifications or embodiments that correlate the output transducer measurements to the tympanic membrane sound pressures are provided or discussed.

What would be useful is an electronic earplug that monitors and replicates sound pressures at the tympanic membrane thereby offering electronic enhanced noise reduction performance at the tympanic membrane over a specific frequency bandwidth. Such an electronic earplug would also provide accurate monitoring; and high-bandwidth noise reduction performance at the tympanic membrane for the required conditions of a hearing protection application. The accurate resemblance, or mapping, of complex sound pressures at the earplug microphone to the complex sound pressures at the tympanic membrane would also permit calculations of noise exposure limits for humans in hazardous noise fields.

SUMMARY OF INVENTION

An embodiment of the present invention is an electronic earplug that provides means to accurately monitor an electronic reduction of acoustic pressures at the tympanic membrane (TM) over a wide range of frequencies. The electronic earplug according to this embodiment, monitors the TM sound pressures, determines an individual's time-intensity noise exposure (dosimetry), and provides ANR noise reduction at the TM at frequencies above 1.5 kHz.

Therefore, an aspect of the present invention is an electronic earplug that provides a high degree of predictable passive noise attenuation at the TM.

It is another aspect of the present invention to incorporate into an electronic earplug transducers located to provide accurate dosimetry of either uncontrolled (open-loop) or electronically controlled (closed-loop) sound pressure levels at the TM surface as well as ensure that any electronic noise reduction delivered to the earplug microphone will correspondingly be delivered to the eardrum and be perceived as actual control over the design bandwidth.

A further aspect of the invention is an electronic earplug that provides accurate dosimetry of the TM noise exposure without simultaneous electronic control.

Yet another aspect of the present invention is to measure electronic noise control attenuation at the earplug microphone location that is the same as the control attenuation at the tympanic membrane over some specified range of frequencies.

Another aspect of the present invention is a method of designing an electronic earplug wherein the method supports the determination of the frequency range over which the ANR control attenuation at the earplug microphone is the same as the ANR control attenuation at the tympanic membrane.

Yet another aspect of the present invention is an electronic earplug that extends the active noise reduction bandwidth to frequencies greater than 1.5 KHz.

DETAILED DESCRIPTION OF THE PRESENT INVENTION

An embodiment of the present invention relates the design features of an electronic earplug and the connectivity of such features to the anatomical features of the occluded ear canal space to the dynamic acoustic impedance at any selected location inside the earplug or ear canal. Prior art electronic earplug designs have not sufficiently addressed those acoustic dynamics. The control attenuation of these prior art designs is not comparable to (and is always greater than) the actual perceived active noise reduction performance achieved at the tympanic membrane. This is especially true at frequencies higher than approximately 1.0 kHz for prior art designs of electronic earplugs. This observation is critical for any noise attenuation goals that relate to either human perception of the control attenuation or hearing safety metrics that involve measurement of exposure (e.g. Occupational Safety and Health Administration (OSHA) calculations of human noise exposure limits). This is because the sound pressure level at the TM is directly proportional to the perceived loudness and the inner ear fatigue associated with hazardous sound pressure levels.

Figure 1:
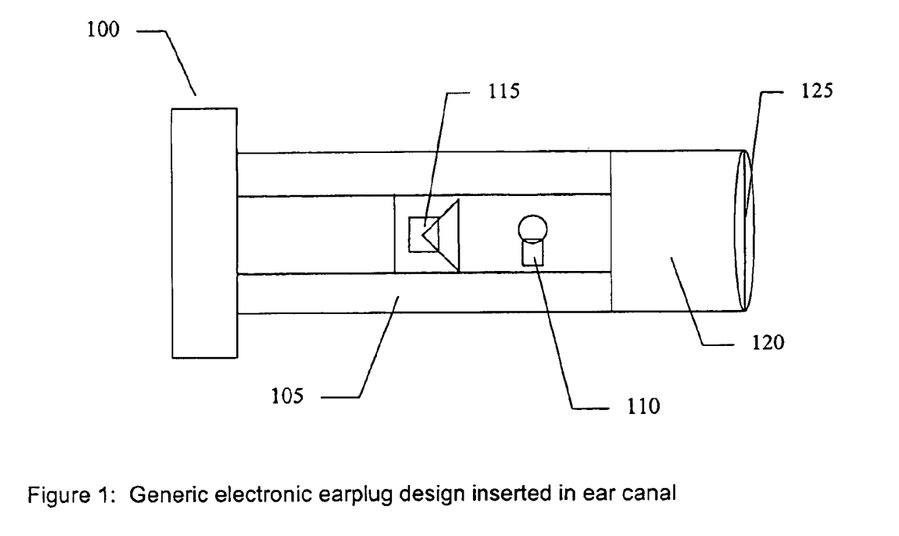
FIG. 1 illustrates an electronic earplug according to an embodiment of the present invention wherein the electronic earplug comprises an acoustic driver and an earplug microphone.

FIG. 1 illustrates an electronic earplug designed according to an embodiment of the present invention to accurately monitor sound pressure at the TM and to provide noise reduction over a wide bandwidth at the TM. Electronic earplug 100 comprises an earplug housing 105, an earplug microphone 110, and an acoustic driver 115. The earplug housing 105 reaches sufficiently into the ear canal 120 to accommodate a position for the earplug microphone 110 to monitor noise exposure at the TM 125 and to provide noise reduction performance at the TM to some determined bandwidth, as discussed below. Acoustic driver 115 provides means for combing electronic control and/or communication with noise monitoring.

In an embodiment, the acoustic driver 115 is a balanced armature hearing aid type receiver and earplug microphone 110 is an electret type transducer. In another embodiment, acoustic driver 115 is a miniaturized voice coil speaker. In still another embodiment, acoustic driver 115 is a piezoelectric speaker. As will be apparent to those skilled in the art, other devices that receive and actuate acoustic energy may be employed to perform the tasks of acoustic driver 115 and earplug microphone 110 without departing from the scope of the present invention.

In yet another embodiment, earplug housing 105 is custom molded to fit the ear canal 120 of a user. In an alternate embodiment, the custom molded portion of the earplug housing 105 is limited to the portion of the housing that extends into the ear canal 120. By way of example and not as a limitation, an earplug housing 105 may be constructed from polyvinylchloride, acrylic, a combination of polyvinylchloride and foam, and a combination of acrylic and foam.

Figure 2:
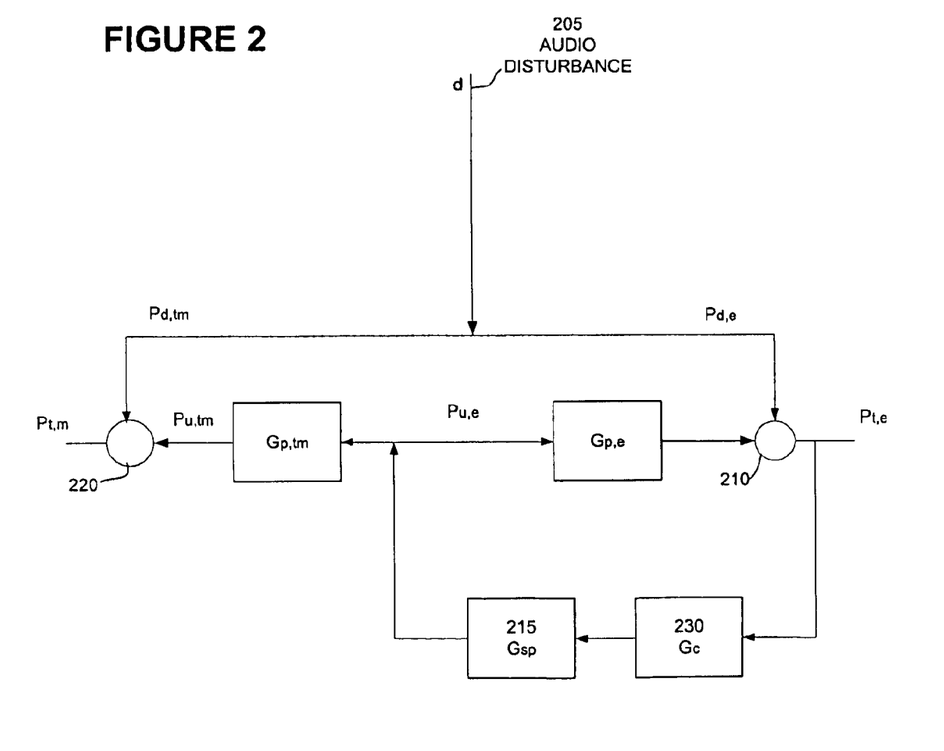
FIG. 2 is a block diagram illustrating the physical relationships between the acoustic driver of an electronic earplug, the ambient noise sound pressure disturbance, the sound pressure in the vicinity of the earplug microphone, and the sound pressure acting on the tympanic membrane according to an embodiment of the present invention.

FIG. 2 is a block diagram illustrating the signal paths in an electronic earplug designed according to an embodiment of the present invention. An audio disturbance 205 impinges on a user of an electronic earplug (see FIG. 1) and the sound pressure associated with audio disturbance (d) is directed to earplug microphone 210 and TM 220. The sound pressure of the audio disturbance at earplug microphone 210 is represented as $P_{d,e}$. The sound pressure of the audio disturbance at TM 220 is represented as $Pd_{tm}$. Earplug microphone 210 is connected to controller 230. Controller 230 connects to acoustic driver 215. Controller 230 is characterized by transfer function $G_c$ and acoustic driver 215 is characterized by transfer function $G_{sp}$. A portion of the output of acoustic driver 215 is fed back to earplug microphone 210 and impinges on tympanic membrane 220. The acoustic dynamics that are excited by acoustic driver 215 are represented by two transfer functions. The acoustic dynamics between acoustic driver 215 and the tympanic membrane are given by transfer function $G_{p,tm}$, while the acoustic dynamics between the acoustic driver 215 and the earplug microphone are represented by transfer function $G_{p,e}$. The combination of the audio disturbance sound pressure $P_{d,e}$ and the control sound pressure $P_{u,e}$ at the earplug microphone 210 forms the total sound pressure $P_{t,e}$ measured by the earplug microphone. The combination of the disturbance sound pressure $P_{d,tm}$ and the control sound pressure $P_{u,tm}$ at the tympanic membrane forms the total sound pressure perceived at the eardrum tympanic membrane $P_{t,tm}$.

Based on the input-output relationships of FIG. 2, the total sound pressure at the surface of the tympanic membrane is described by Equation 1 below:

$$P_{t,tm} = P_{d,tm} + P_{u,tm} = P_{d,tm} + \frac{G_c G_{sp} G_{p,tm}}{1 - G_c G_{sp} G_{p,e}} P_{d,e} \quad \text{(Eq 1)}$$

Thus, the total sound pressure level perceived at the surface of the tympanic membrane is related to two different noise generation mechanisms, one from the feedback acoustic signal emitted acoustic driver 215, causing sound pressure $P_{u,tm}$, and one from the external disturbance noise, causing sound pressure $P_{d,tm}$. By considering each term more carefully, it can be observed that $P_{d,tm}$ is the sound pressure field at the tympanic membrane after the passive control of the electronic earplug 200 has been applied, and $P_{u,tm}$ is the sound pressure at the tympanic membrane from the active noise controller design.

One critical observation is that this expression for the sound pressure at the TM is considerably different than the equations used for design of electronic earplugs in prior art. Prior art typically assumes that the noise field being controlled at the earplug's microphone (FIG. 1,110 and FIG. 2,210) is identical to that at the TM (FIG. 1,125 and FIG. 2, 220). This design approach incorrectly assumes that the total sound pressure at the TM 220 (due to disturbance and control) will be reduced by a controller having a transfer function $G_c$ in accordance with Equation 2:

$$P_{t,e} = \frac{1}{1 - G_c G_{sp} G_{p,e}} P_{d,e} \quad \text{(Eq. 2)}$$

Prior art designs based on minimizing the sound pressure expression of Equation 2 only results in minimization of the total complex sound pressure $P_{t,e}$ at the earplug microphone 210 and not at the TM 220 where the control is truly desired.

Although Equation 2, derived from FIG. 2 is true at the earplug microphone, satisfying the expression of Equation 2 does not assure that the total sound pressure at the tympanic membrane $P_{t,tm}$ will be minimized. An embodiment of the present invention utilizes the information presented in Equation 1 to design and construct electronic earplugs using active noise control to achieve effective electronic noisy reduction performance at the TM location for known bandwidths and to provide earplug microphone sound pressure measurements that accurately monitor the TM sound pressure (accurate dosimetry) for both open loop and/or closed loop.

Equation 1 represents the closed loop expression for the sound pressure at the TM. This expression can be rewritten as the ratio between the total sound pressure at the tympanic membrane $P_{t,tm}$ and the disturbance-generated sound pressure $P_{d,tm}$ (since the disturbance generated sound pressure at the earplug microphone $P_{d,e}$ is largely equal to the disturbance generated sound pressure at the TM $P_{d,tm}$):

$$\frac{P_{t,tm}}{P_{d,tm}} = 1 - \frac{G_{p,tm} G_c G_{sp}}{1 - G_c G_{sp} G_{p,e}} \quad \text{(Eq 3)}$$

Equation 2 illustrates the relationship of the closed-loop complex sound pressure at the earplug microphone to the disturbance-induced complex sound pressure at the earplug microphone while Equation 3 illustrates the relationship of the closed-loop complex sound pressure at the TM to the disturbance-induced complex sound pressure at the TM.

An embodiment of the present invention is a method of designing an electronic earplug that provides control attenuation at the eardrum. This embodiment achieves such control attenuation by minimizing the result of Equation 3 directly through design of a frequency response function associated with transfer function $G_c$ of the feedback controller 230 so as to affect frequency response functions associated with transfer functions $G_{p,tm}$ and $G_{p,e}$. In this embodiment, placement of the acoustic driver 215 and earplug microphone 210 define these frequency response functions. If there are no considerations given to the placement acoustic driver 215 and earplug microphone 210, then transfer functions $G_{p,tm}$ and $G_{p,e}$ can be considered to be arbitrary. For such a case, the frequency response function associated with transfer function $G_c$ of controller 230 is designed to minimize Equation 3 using a feedback control design technique that targets minimizing broadband disturbance. By way of illustration and not as a limitation, controller 230 uses a loop-shaping method or an optimal method of feedback control. One advantage of this embodiment is that acoustic driver 215 and earplug microphone 210 can be placed virtually anywhere in the earplug, and the controller design can ensure designed electronic noise reduction performance at the tympanic membrane. However, the measured electronic noise reduction performance at the earplug microphone 210 will not reflect the realized noise reduction performance at the TM 220. Even so, this embodiment represents an improvement over prior art electronic earplug designs that focused only on minimizing the sound pressure expression of Equation 2.

Another embodiment of the present invention is to place the acoustic driver 215 and earplug microphone 210 so as to define the frequency response of transfer functions $G_{p,tm}$ and $G_{p,e}$ to provide the same control bandwidth at the TM as at the earplug microphone 210 while designing transfer function $G_c$ of controller 230 such that its frequency response minimizes the result of Equation 2. This embodiment focuses on design and constructing an electronic earplug in such a way that will ensure that perceived electronic noise reduction performance at the TM 220 is the same as the measured electronic noise reduction performance at the earplug microphone 210 by governing the specific placement of the acoustic driver 215 and earplug microphone 210 in the electronic earplug 200.

Using this embodiment, the earplug microphone 210 is positioned in the electronic earplug 100 such that it is mathematically similar to the TM 220 in its acoustic impedance over some bandwidth. In general, the complex ratio $$\frac{G_{p,tm}}{G_{p,e}}$$

depends on the specific location of the earplug microphone 210 inside the electronic earplug 200 that will in turn be dependent on the construction of the earplug itself. It is helpful but not sufficient that this ratio equals unity over as large a frequency bandwidth as possible. If the two transfer functions are exactly equal, Equation 3 becomes Equation 2. (This occurrence rarely happens in practice, and only over a very small bandwidth).

Figure 3:
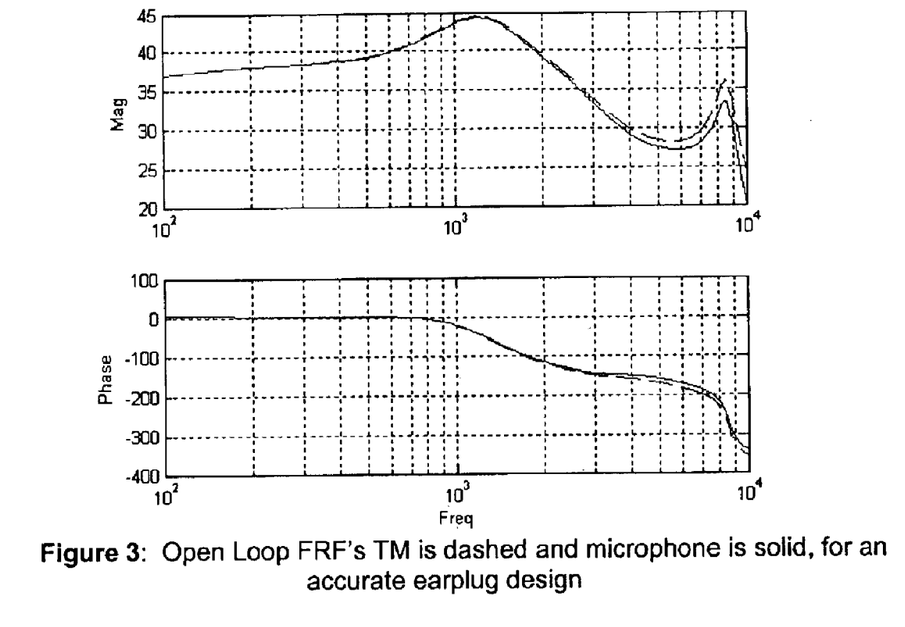
FIG. 3 illustrates the closed-loop electronic noise reduction at the tympanic membrane for a typical electronic earplug according to an embodiment of the present invention in which the loop gain of the feedback control system is high relative to unity.
Figure 4:
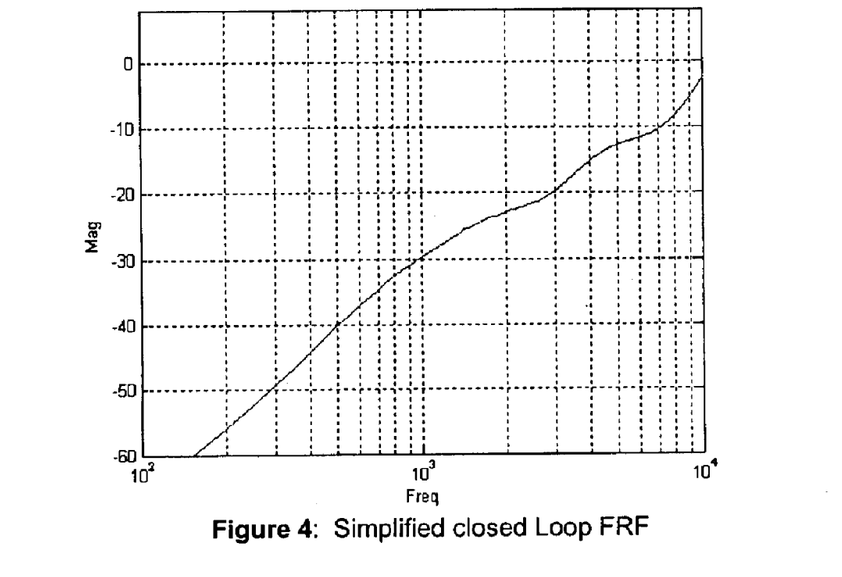
FIG. 4 illustrates the closed-loop electronic noise reduction at the tympanic membrane for an electronic earplug according to the embodiment of the present invention in which the loop gain of the feedback control system is not High relative to unity.

FIGS. 3 and 4 illustrate how the frequency response functions associated with transfer functions $G_{p,tm}$ and $G_{p,e}$ for a typical electronic earplug affect the design methods according to this invention.

FIG. 3 illustrates the complex-valued frequency response functions associated with transfer functions $G_{p,tm}$ and $G_{p,e}$, in magnitude and phase units for an electronic earplug designed according to an embodiment of the present invention. In this embodiment, the open loop magnitude and phase are nearly identical over a certain bandwidth as a result of the placement of acoustic driver 115 and earplug microphone 110. If the open loop magnitude is much greater than unity, this embodiment will produce a closed-loop electronic noise reduction performance at the TM as illustrated in FIG. 4.

Figure 5:
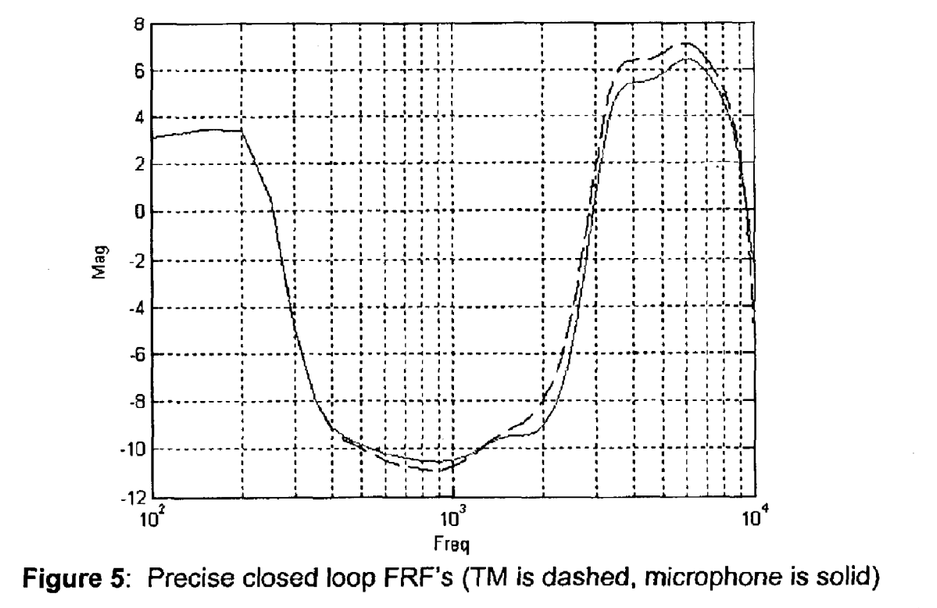
FIG. 5 is a comparison of the TM and the earplug microphone closed loop complex pressures in an embodiment of the present invention.

In most cases, it is not possible to design the loop gain to be much greater than unity (which implies very high closed loop attenuation) and a more general result follows from Equation 3. FIG. 5 compares the closed-loop electronic noise reduction performance at the TM to the electronic noise reduction performance at the earplug microphone, based on the calculation of Equation 3, for the same earplug design illustrated in FIGS. 3 and 4. The differences in TM closed-loop performance between FIG. 4 and FIG. 5 are due to the additional dependence on $G_c$ which has a low loop gain. FIG. 5 illustrates that as result of the design process of this embodiment of the present invention, the TM electronic noise reduction performance is approximately identical to the electronic noise reduction at the earplug microphone up to a frequency of approximately 3 kHz.

Figure 6:
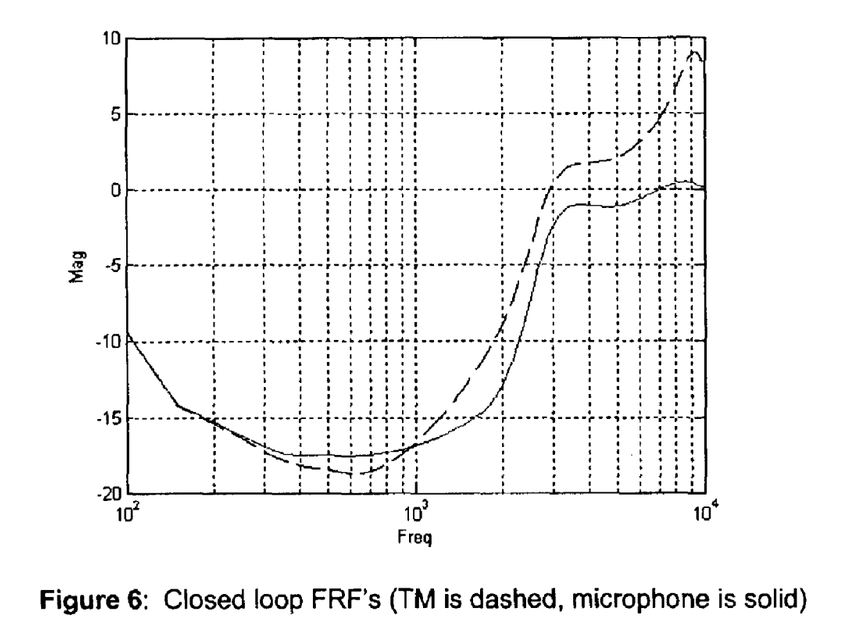
FIG. 6 illustrates a comparison of the total closed loop sound pressure at the TM to the total closed loop sound pressure at the earplug microphone for an electronic earplug designed according to an embodiment of the present invention.
Figure 7:
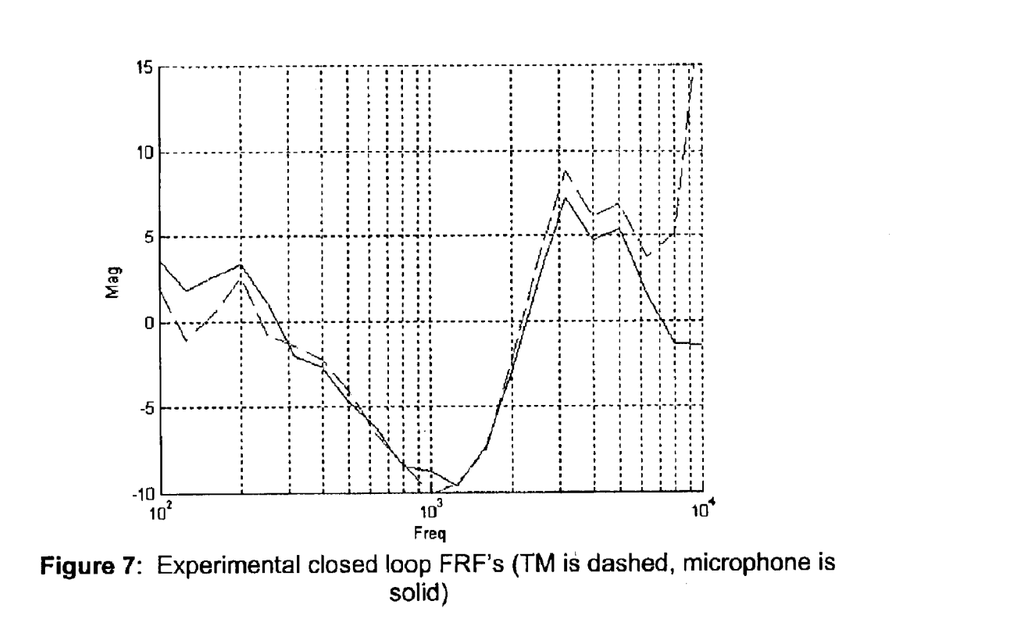
FIG. 7 illustrates experimentally measured data for an electronic earplug designed according to an embodiment of the present invention.

As previously noted, an objective of the present invention is knowledge of the complex sound pressure at the TM. The total TM sound pressure $P_{t,tm}$ may be identified in any number of ways known to those skilled in the art. Identification methods include direct measurement with a probe that extends to the immediate vicinity of the tympanic membrane, or estimation methods based on a one-dimensional acoustic model of the occluded acoustic spaces after insertion of an earplug, or higher-order dimensional models created using analytical or finite element modeling techniques that are well known to acousticians. By way of illustration and not as a limitation, FIG. 6 illustrates a one-dimensional acoustic model according to an embodiment of the present invention. In this embodiment, the transfer function $\hat{G}_{p,tm}=G_{p,tm}$ is used for the identification of $P_{t,tm}$ versus $P_{t,e}$. FIG. 6 illustrates how the total closed loop sound pressure at the TM (dotted trace) can compare to the total closed loop sound pressure at the earplug microphone (solid trace) for one possible electronic earplug design, when using the one-dimensional acoustic information. FIG. 7 illustrates the experimentally measured comparison of the same quantities (tympanic membrane sound pressure dashed), illustrating the adequacy of this particular TM pressure identification technique for the invention. In each of these cases it is important to note that the design was carried out (in simulation and experiment) to ensure that the control bandwidth was the same for the tympanic membrane as it was for the earplug microphone. As predicted by Equation 3, if the design is not carefully considered for the whole bandwidth, the tympanic membrane sound pressure can significantly deviate from the earplug microphone sound pressure as occurs in both simulation and experiment in higher frequencies of FIGS. 6 and 7.

As previously described, it is important to consider earplug microphone placement if the electronic earplug design is to achieve the same electronic noise reduction performance at the earplug microphone and the tympanic membrane. As a general rule, the TM electronic noise reduction performance illustrated in FIG. 5 requires that the earplug microphone and the TM be as close to monophase and equal magnitude conditions for as large a frequency band as possible within the geometrical constraints of an earplug user's ear canal dimensions. This depends on the occluded space acoustic dynamics only (ear canal and any exposed volumes inside the earmold) and not the electromechanical transducers' dynamics.

Figure 8:
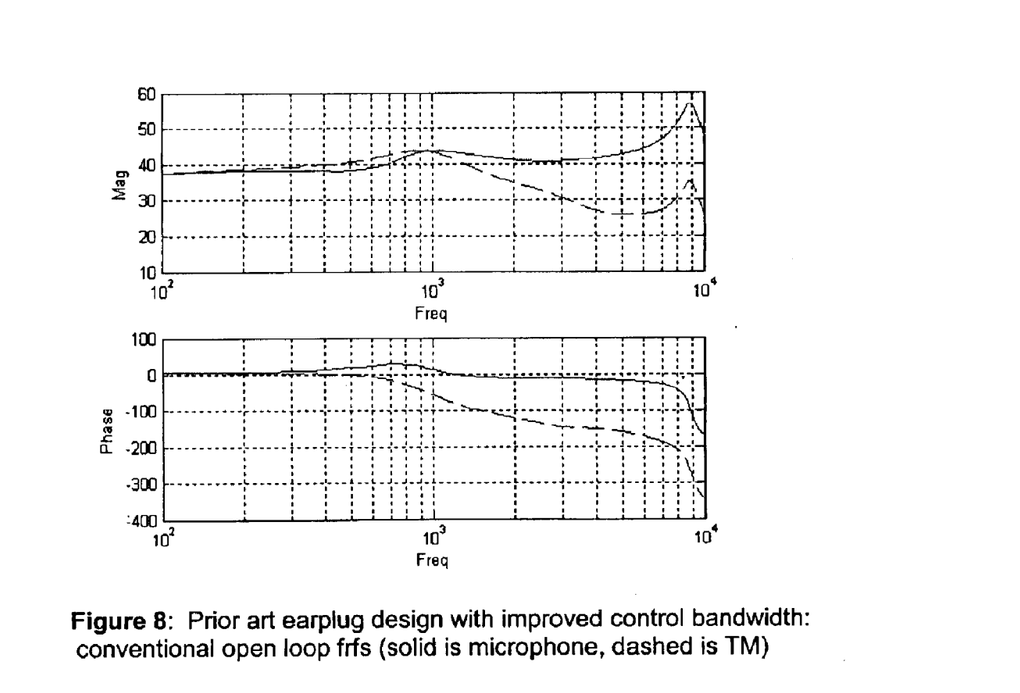
FIG. 8 illustrates a comparison of two frequency response functions determined from an electronic earplug typical of the prior art.
Figure 9:
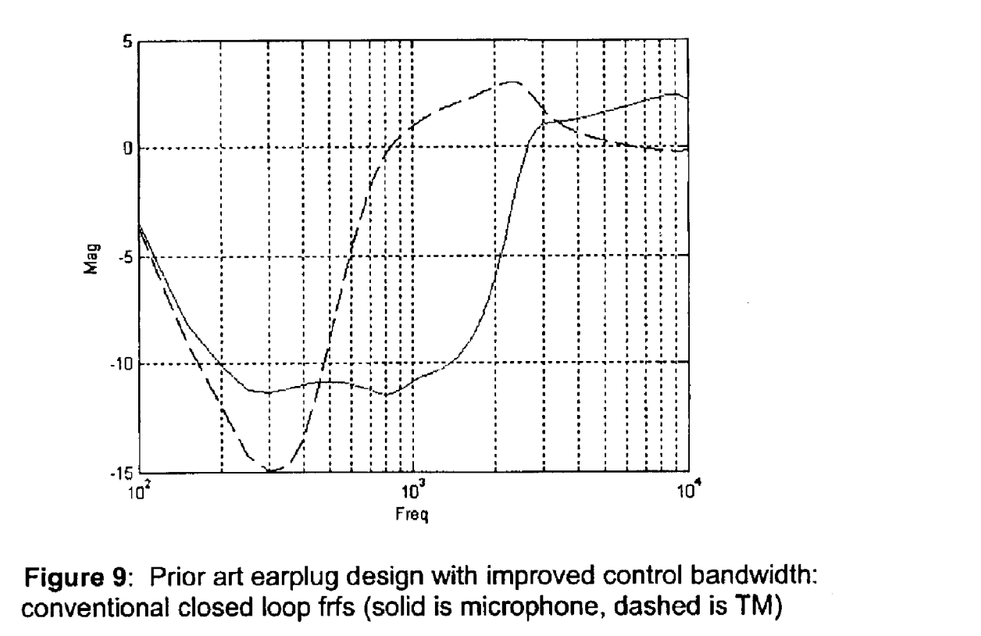
FIG. 9 illustrates a comparison of corresponding closed loop total pressures at the TM and the earplug microphone for a controller designed to minimize sound pressure at the earplug microphone location of an electronic earplug designed according to the prior art.
Figure 10:
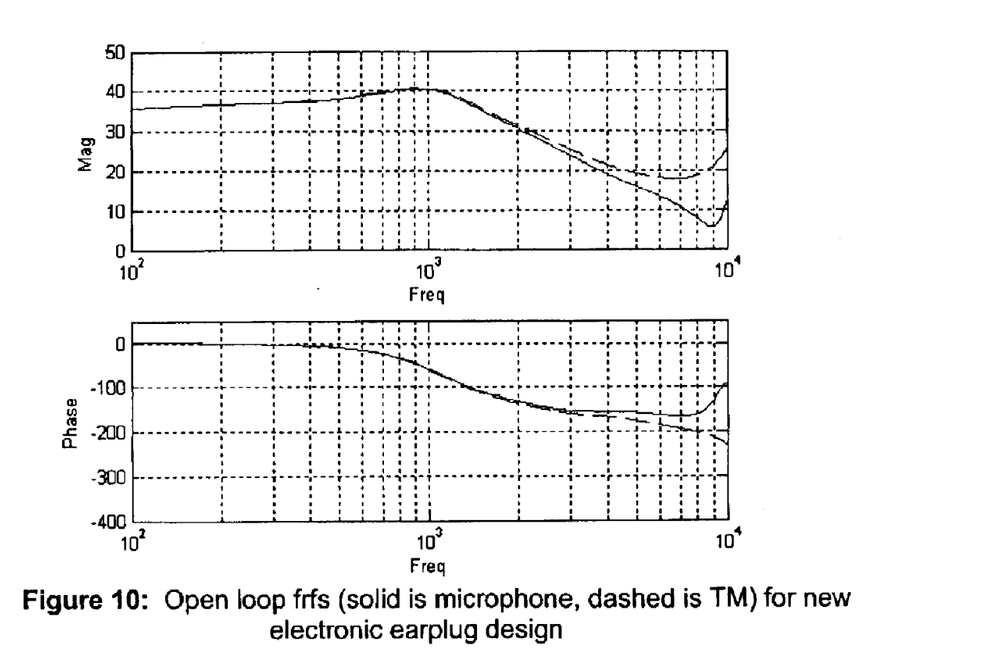
FIG. 10 illustrates a comparison of two open loop frequency response functions of an electronic earplug designed in accordance with an embodiment of the present invention.
Figure 11:
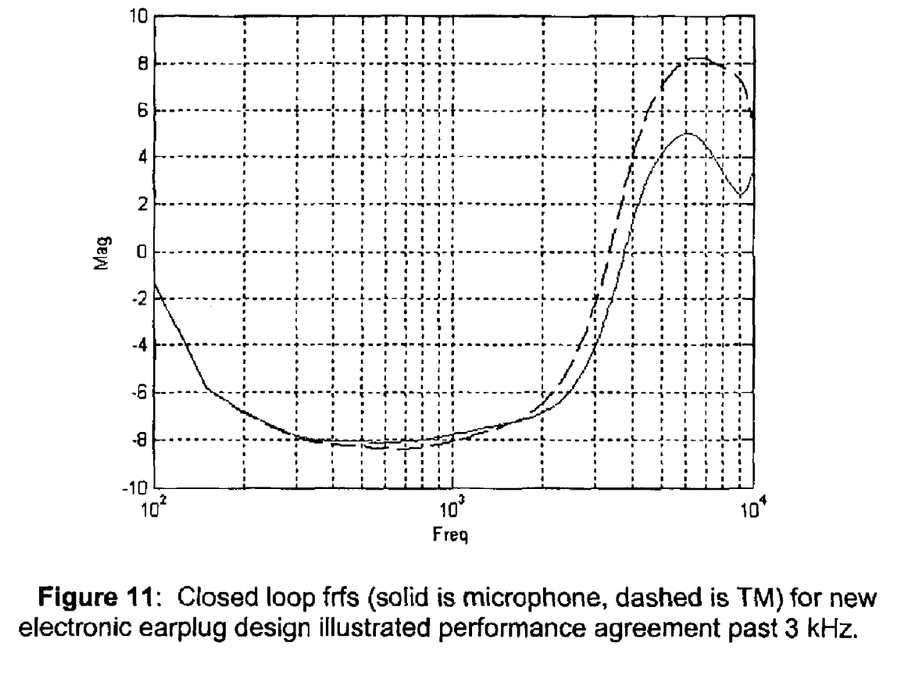
FIG. 11 illustrates a comparison between the closed loop total sound pressure at the TM and the earplug microphone for an electronic earplug designed in accordance with an embodiment of the present invention.

An embodiment of the present invention locates an earplug microphone and acoustic driver in an earplug based on the frequency of the occluded space acoustic half-wave resonance that occurs nominally above 8 kHz. By way of example, FIGS. 8–11 illustrate the affects of varying the earplug microphone position. In particular, FIGS. 8 and 9 illustrate the electronic noise reduction performance of electronic earplugs designed according to the prior art. FIGS. 10 and 11 illustrate the electronic noise reduction performance of electronic earplugs designed according to embodiments of the present invention wherein the tympanic membrane electronic noise reduction performance is equal to the electronic microphone electronic noise reduction performance over bandwidths at least up to 2 kHz, based on the design formulation presented above through Equation 3.

FIG. 8 is a comparison of two frequency response functions determined from an electronic earplug typical of the prior art. A dashed trace reflects the frequency response function of a speaker in the concha area of a custom-molded electronic earplug and the complex sound pressure at the surface of the TM. A solid trace reflects the frequency response function between the same speaker in the same concha area and an adjacent microphone location in the concha area. This electronic earplug construction is typical of prior art electronic noise canceling earplug designs where there is no effort or consideration made to locating the earplug microphone in the earplug to ensure commensurate electronic noise reduction performance at the TM. Both the magnitudes and phases of these frequency response functions quantitatively diverge at frequencies above 1 kHz.

A unique controller design process was then employed to obtain attenuation performance to 2.5 kHz at the earplug microphone. (Prior an controller designs have not been able to achieve this bandwidth even at the earplug microphone). This improved controller design process was carried out using a frequency response function derived by minimizing Equation 2. FIG. 9 compares the corresponding closed loop total pressures at the TM (dashed trace) and the earplug microphone (solid trace, based on Equation 3) for a controller designed to minimize sound pressure at the earplug microphone location. This design process is entirely consistent with and described in prior art (although the bandwidth realized at the earplug microphone in this example exceeds any prior an discussions of control bandwidth).

As illustrated by FIG. 9, this prior art electronic earplug design does not meet the wideband closed loop performance at the tympanic membrane enabled by embodiments of the present invention. Although the electronic noise reduction performance was designed to minimize the sound pressure at the earplug microphone up to 2.5 kHz, the attenuation perceived at the tympanic membrane never exceeds a frequency of 800 Hz. This particular earplug design, consistent with typical prior electronic earplug art, employs a speaker and an earplug microphone in the concha of the earplug. Such a design, when coupled with a high passive control electronic earplug, cannot provide wideband attenuation at the TM.

FIG. 10 is a comparison of two open loop frequency response functions of an electronic earplug designed in accordance with an embodiment of the present invention. A dashed trace represents a first frequency response function between a speaker in the concha and the TM. A solid trace represents a second frequency response function between a speaker in the concha area of an electronic earplug and an earplug; microphone location further down the earplug, at a design location selected to match the first frequency response function between 0 and 4 kHz. The exact location of the earplug microphone is dependent on the location of the speaker, the acoustic dynamics in the electronic earplug itself, and the shape of the controller. It is not simply sufficient to place the earplug microphone in front of the speaker, nor is it sufficient to state that it must be within a certain distance of the speaker, or tip of the electronic earplug. Instead, in order to ensure that the electronic noise reduction performance reaches the TM, the design process described in reference to Equation 3 must be used. Equation 3 summarizes that design process either for the controller, or the electronic earplug as a system.

FIG. 11 illustrates the corresponding closed loop performance comparisons between the closed loop total sound pressure at the TM (dashed trace) and the earplug microphone (solid trace), illustrating wideband (up to 3 kHz) closed loop performance at the TM. FIG. 11 validates the design process of the present invention and demonstrates that placing the specific components of the electronic earplug in accordance with the embodiments of the present invention provides substantially the same electronic noise reduction performance at the TM that is achieved at the earplug microphone. This is contrasted with prior art earplug designs that generate the performance shown in FIGS. 8 and 9, where component placement prevents tympanic membrane control beyond 800 Hz.

As is known in the art, the open loop characteristics described herein are determined with $G_c$ equal to zero. For dosimetry, or accurate monitoring of sound pressure at the eardrum, the goal is simply to determine accurately the magnitude of the sound pressure at the TM over the desired bandwidth of accuracy for either closed loop or open loop operation. Depending on the acceptable tolerance of the dosimetry measurement, the magnitude may deviate from an exact equality over certain frequency bands and still provide an accurate dosimetry calculation. The phase agreement between the open loop and closed loop transfer functions is not critical to achieve an accurate amplitude measurement used in dosimetry. Therefore, the open loop FRF comparisons presented in FIGS. 8 and 10 are illustrative of the reliability of predicting the TM sound pressures based on placement of the earplug microphone.

In addition, it has been illustrated that the methods used to identify the TM sound pressures (i.e. determination of $G_{p,tm}$) are sufficiently accurate such that either open loop or closed loop values of the TM sound pressure levels can be reliably predicted for any frequency range desired. Therefore, it is possible to utilize information from an earplug microphone placed at any location within an electronic earplug to calibrate the measured levels against the predicted levels (using the acoustic models described earlier for either open loop or closed loop) for accurate estimation, and subsequent monitoring, of the TM sound pressures. For example, the actual open loop exposure at the tympanic membrane can be computed using knowledge of the control to earplug microphone path frequency response magnitude and the control to TM frequency response magnitude. The difference in the magnitudes of these frequency response functions forms a frequency dependent calibration factor that is applied to noise measured at the earplug microphone to determine the estimated TM exposure. Equation 4 illustrates this concept.

$$EstimatedOpenLoopTM \text{ pressure} = (|G_{p,tm}| - |G_{p,e}|) + |P_{t,e}| \qquad (Eq\ 4)$$

Here the magnitude of the sound pressure measured at the earplug microphone is modified by the difference in magnitudes of the transfer functions between the frequency responses to arrive at an estimate of the actual sound pressure at the tympanic membrane, based on the measured earplug microphone signal.

Similarly, this calibration for dosimetry can be performed when an electronic earplug is operating in closed loop for additional noise attenuation. The calibration factor itself is modified by the closed loop nature of the system and can be represented by Equation 5.

$$EstimatedClosedLoopTM\ \text{pressure} = \qquad (\text{Eq 5})$$

$$\left(\left|\frac{1 - G_{p,e}G_{sp}G_c + G_{p,tm}G_{sp}G_c}{1 - G_{p,e}G_{sp}G_c}\right| - \left|\frac{1}{1 - G_{p,e}G_{sp}G_c}\right|\right) + |P_{t,e}|$$

Therefore, embodiments of the invention have been shown that enable the ability to conduct electronic control of sound pressure at the TM for a wide range of frequency, while simultaneously monitoring the sound pressures at the TM for all frequencies, based on the relationships and methodologies presented above. It is clear that the overall invention may include many types of earplug materials, acoustic driver designs, microphone designs and feedback control algorithms without deviating from the scope discussed herein.

What is claimed is:

1. A method for designing an electronic earplug, wherein the electronic earplug comprises an outer housing that extends into as ear canal to approximately the second bend and accommodates an acoustic driver and a transducer for measuring acoustic sound, and wherein the acoustic driver is located between a concha and the transducer and the transducer is located in an ear canal, the method comprising:

determining a first complex sound pressure at the tympanic membrane;

determining a second complex sound pressure at the transducer; and locating the transducer within the outer housing until the first complex sound pressure and the second complex sound pressure are substantially equal at frequencies up to 5 KHz., and wherein the first complex sound pressure at the tympanic membrane is determined using a probe situated to monitor the second complex sound pressure at a location in the ear canal away from the tympanic membrane, and wherein the first complex sound pressure is related to the second complex sound pressure by a transfer function determined using a means for emulating an ear canal and a tympanic membrane.

2. The method for designing an electronic earplug as in claim 1, wherein the means for emulating an ear canal and a tympanic membrane is selected from the group consisting of a one-dimensional transmission line acoustic model of the ear canal and tympanic membrane, a two-dimensional acoustic model of the ear canal and tympanic membrane, a three-dimensional acoustic model of the ear canal and tympanic membrane, a boundary element model of the ear canal and tympanic membrane, a finite element model of the ear canal and tympanic membrane, and an electrical analogue model of the ear canal and tympanic membrane.

3. A method for designing an electronic earplug wherein the electronic earplug comprises an outer housing that extends into an ear canal to approximately the second bend and accommodates an acoustic driver and a transducer for measuring acoustic sound, and wherein the acoustic driver is located between a concha and the transducer and the transducer is located in an ear canal, the method comprising:

determining a first complex sound pressure at the tympanic membrane;

determining a second complex sound pressure at the transducer; and locating the transducer within the outer housing until the first complex sound pressure and the second complex sound pressure are substantially equal at frequencies up to 5 KHz., and wherein the first complex sound pressure at the tympanic membrane is determined using a probe situated to monitor the pressure adjacent to the surface of means for emulating an ear canal and a tympanic membrane.

4. The method for designing an electronic earplug as in claim 3, wherein the means for emulating an ear canal and a tympanic membrane is selected from the group consisting of a one-dimensional transmission line acoustic model of the ear canal and tympanic membrane, a two-dimensional acoustic model of the ear canal and tympanic, membrane, a three-dimensional acoustic model of the ear canal and tympanic membrane, a boundary element model of the ear canal and tympanic membrane, a finite element model of the ear canal and tympanic membrane, and an electrical analogue model of the ear canal and tympanic membrane.

5. A method for designing an electronic earplug wherein the electronic earplug comprises an outer housing that extends into an ear canal to approximately the second bend and accommodates as acoustic driver and a transducer for measuring acoustic sound, and wherein the acoustic driver is located between a concha and the transducer and the transducer is located in an ear canal, and a controller, wherein the controller is connected to the transducer and the acoustic driver, the method comprising:

determining a closed loop transfer function, wherein the closed loop transfer function associates a total sound pressure at the tympanic membrane and a first sound pressure at the tympanic membrane resulting from an acoustic signal external to the outer housing;

measuring a second sound pressure proximal to the location of the acoustic driver using the transducer;

generating an audible control signal at the controller based on the second sound pressure at the location of the acoustic driver wherein the audible control signal is generated so as to minimize the closed loop transfer function; and applying the audible control signal to the acoustic driver to minimize the closed loop transfer function between the total sound pressure at the tympanic membrane and the second sound pressure at the tympanic membrane resulting from the acoustic signal external to the outer housing.

6. The method for designing an electronic earplug as in claim 5, wherein the acoustic driver is selected from the group consisting of a dynamic voice coil speaker, a balanced armature receiver, and a piezoceramic device.

7. The method for designing an electronic earplug as in claim 5, wherein the transducer is selected from the group consisting of an electret microphone, a piezoelectric microphone, and a micro-machined silicon-based microphone.

8. The method for designing an electronic earplug as in claim 5, wherein the controller comprises a feedback device.

9. The method for designing an electronic earplug as in claim 5, wherein the controller comprises a feedforward device.

10. A method for predicting the open-loop sound pressure at a tympanic membrane using an electronic earplug, wherein the electronic earplug comprises an outer housing that extends into am ear canal and accommodates an acoustic driver and a transducer for measuring acoustic sound, and wherein the acoustic driver is located between a concha and the transducer and the transducer is located in an ear canal, the method comprising:

determining a first open-loop frequency response function over a bandwidth of all audible frequencies, wherein the first open-loop frequency response function represents the open-loop acoustic dynamics between the acoustic driver and the earplug microphone;

determining a second open loop frequency response function over a bandwidth of all audible frequencies, wherein the second open loop frequency response function represents the open-loop acoustic dynamics between the acoustic driver and the sound pressure at the tympanic membrane;

calculating an open-loop calibration difference equal to the magnitude of the difference between the first open-loop frequency response function and the second open-loop frequency response function over a bandwidth of all audible frequencies; and predicting the open-loop sound pressure at the tympanic membrane at a specific audible frequency by applying the open-loop calibration difference at the specific frequency to the magnitude of the sound pressure measured by the transducer at that specific audible frequency.

11. The method for the predicting the open-loop sound pressure at the tympanic membrane using an electronic earplug as in claim 10, wherein predicting the open-loop sound pressure at a specific audible frequency by applying the open-loop calibration difference at the specific frequency to the magnitude of the sound pressure measured by the transducer at that specific audible frequency comprises monitoring sound exposure at the tympanic membrane.

12. The method for the predicting the open-loop sound pressure at the tympanic membrane using an electronic earplug as in claim 10, wherein the acoustic driver is selected from the group consisting of a dynamic voice coil speaker, a balanced armature receiver, and a piezoceramic device.

13. The method for the predicting the open-loop sound pressure at the tympanic membrane using an electronic earplug as in claim 10, wherein the transducer is selected from the group consisting of an electret microphone, a piezoelectric microphone, and a micro-machined silicon-based microphone.

14. A method for the predicting the sound pressure at a tympanic membrane during active noise control using an electronic earplug wherein the electronic earplug comprises an outer housing that wands into an ear canal and accommodates an acoustic driver and a transducer for measuring acoustic sound, and wherein the acoustic driver is located between a conchs and the transducer and the transducer is located in an ear canal, and a controller, wherein the controller is connected to the acoustic driver, the method comprising:

sizing the outer housing to provide decoupling of acoustic paths between an acoustic signal originating external to the outer housing and a tympanic membrane;

determining a first closed-loop complex frequency response function over a bandwidth of all audible frequencies, wherein the first closed-loop frequency response function represents the electro acoustic dynamics between the controller and the acoustic driver and between the acoustic driver and the sound pressure at the transducer;

determining a second closed loop complex frequency response function over a bandwidth of all audible frequencies, wherein the second closed loop frequency response function represents the electro acoustic dynamics between the controller and acoustics driver and between the acoustic driver and the sound pressure at the tympanic, membrane;

calculating a closed-loop calibration difference equal to the magnitude of the difference between the first complex closed-loop frequency response function, and the second complex closed-loop frequency response function over a bandwidth of all audible frequencies; and predicting the closed-loop sound pressure at the tympanic membrane at a specific audible frequency by applying the closed-loop calibration difference at the specific frequency to the magnitude of the sound pressure during noise control measured by the transducer at that specific audible frequency.

15. The method for the predicting the sound pressure at a tympanic membrane during active noise control using an electronic earplug as in claim 14, wherein the controller comprises a feedback device.

16. The method for the predicting the sound pressure at a tympanic membrane during active noise control using an electronic earplug as in claim 14, wherein the controller comprises a feedforward device.

17. The method for the predicting the sound pressure at a tympanic membrane during active noise control using an electronic earplug as in claim 14, wherein determining a first closed-loop complex frequency response function and determining a second closed loop complex frequency response function comprising using a means for emulating the ear canal and tympanic membrane.

18. The method for the predicting the sound pressure at a tympanic membrane during active noise control using an electronic earplug as in claim 14, wherein the means for emulating a tympanic membrane is selected from the group consisting of a one-dimensional transmission line acoustic model of the ear canal and tympanic membrane, a two-dimensional acoustic model of the ear canal and tympanic membrane, a three-dimensional acoustic model of the ear canal and tympanic membrane, a boundary element model of the ear canal and tympanic membrane, a finite element model of the ear canal and tympanic membrane, and an electrical analogue model of the ear canal and tympanic membrane.

19. The method for the predicting the sound pressure at a tympanic membrane during active noise control using an electronic earplug as in claim 14, wherein predicting the closed-loop sound pressure at the tympanic membrane at a specific audible frequency by applying the closed-loop calibration difference at the specific frequency to the magnitude of the sound pressure during control measured by the transducer at that specific audible frequency comprises monitoring sound exposure at the tympanic membrane.

20. The method for the predicting the sound pressure at a tympanic membrane during active noise control using an electronic earplug as in claim 14, wherein the acoustic driver is selected from the group consisting of a dynamic voice coil speaker, a balanced armature receiver, and a piezoceramic device.

21. The method for the predicting the sound pressure at a tympanic membrane during active noise control using an electronic earplug as in claim 14, wherein the transducer is selected from the group consisting of an electret microphone, a piezoelectric microphone, and a micro-machined silicon-based microphone.

22. A method for designing an electronic earplug wherein the electronic earplug comprises an outer housing that extends into an ear canal to approximately the second bend and accommodates an acoustic driver and a transducer for measuring acoustic sound, wherein the acoustic driver is located between a concha and the transducer and the transducer is located in an ear canal and wherein the acoustic driver is characterized by a transfer function Gsp, anchoring means for the acoustic driver and the transducer, and a controller, wherein the controller is connected to the transducer and the acoustic driver and is characterized by a transfer function Gc, the method comprising:

sizing the outer housing to provide decoupling of acoustic paths between an acoustic signal originating external to the outer housing and a tympanic membrane; and locating the transducer within the ear canal by:
determining a first open-loop transfer function Gp,e between the acoustic driver and the sound pressure at the location of the transducer;
determining a second open-loop transfer function Gp,tm between the acoustic driver and the complex sound pressure at the surface of the tympanic membrane; determining a sound pressure at the transducer Pd,e resulting from an acoustic signal external to the outer housing;
determining a sound pressure at the tympanic membrane Pd,tm resulting from the external acoustic signal;
determining a first complex closed loop frequency response function at the transducer defined by, wherein Pt,e is the total sound pressure at the transducer and wherein Pd,e is the sound pressure at the transducer resulting from an acoustic signal external to the outer housing;
determining a second complex closed-loop frequency, response function at the tympanic membrane defined by, wherein Pt,tm is the total sound pressure at the tympanic membrane and Pd,tm is the sound pressure at the tympanic membrane resulting from an acoustic signal external to the outer housing; and
specifying a fixed location for the transducer such that the first complex closed-loop frequency response function and the second complex closed-loop frequency response function are approximately equal over a specified bandwidth and that Fix is less than the open-loop sound pressure at the tympanic membrane over the specified bandwidth.

23. The method for designing an electronic earplug as in claim 22, wherein the acoustic driver is selected from the group consisting of a dynamic voice coil speaker, a balanced armature receiver, and a piezoceramic device, 24. The method for designing an electronic earplug as in claim 22, wherein the transducer is selected from the group consisting of an electret microphone, a piezoelectric microphone, and a micro-machined silicon-based microphone.

25. The method for designing an electronic earplug as is claim 22, wherein the method further comprises:
calculating a closed-loop calibration difference equal to the magnitude of the difference between the first closed-loop frequency response function and the second frequency response function over a bandwidth of all audible frequencies; and
determining the magnitude of Pt,tm at a specific audible frequency, by applying the closed-loop calibration difference value for that specific audible frequency to the sound pressure measured by the transducer at that specific audible frequency.

26. The method for designing an electronic earplug as in claim 22, wherein the outer housing is at least in part custom-molded.

27. The method for designing an electronic earplug as in claim 22, wherein the outer housing comprises a combination custom-molded earplug base connected to a generic foam tip portion.

28. The method for designing an electronic earplug as in claim 22, wherein the outer housing is constructed from a material selected from the group consisting of polyvinylchloride, acrylic, a combination of polyvinylchloride and foam, and a combination of acrylic and foam.

29. The method for designing an electronic earplug as in claim 22, wherein the anchoring means for the transducer is a fixed attachment to the inner wall of the outer housing.

30. The method for designing an electronic earplug as in claim 22, wherein the anchoring means for the transducer is a fixed attachment at a distal end of a tube connecting the output of the acoustic driver to the transducer.

31. The method for designing an electronic earplug as of claim 22, wherein the controller comprises a feedback device.

32. The method for designing an electronic earplug as in claim 22, wherein the controller comprises a feedforward device.

33. An electronic earplug assembly comprising an outer housing, an acoustic driver for creating acoustic sound, and a transducer for measuring acoustic sound, and a controller, wherein the electronic earplug assembly is characterized by a closed loop transfer function, wherein closed loop transfer function associates a total sound pressure at the tympanic membrane and a first sound pressure at the tympanic membrane resulting from an acoustic signal external to the outer housing, and wherein:
the outer housing is adapted to decouple an acoustic path between the acoustic signal external to the outer housing and the tympanic membrane; and
the transducer is adapted to measure a second sound pressure proximal to the location of the acoustic driver; and
the controller is adapted to:
generate a control signal based on the second sound pressure wherein the audible control signal is generated to minimize the cloned loop transfer function; and
apply the control signal to the acoustic driver to minimize the closed loop transfer function between the total sound pressure at the tympanic membrane and the second sound pressure at the tympanic membrane resulting from the acoustic signal external to the outer housing.

34. The electronic earplug assembly of claim 33, wherein the outer housing is at least in part custom-molded.

35. The electronic earplug assembly of claim 33, wherein the outer housing comprises a combination custom-molded earplug base connected to a generic foam tip portion.

36. The electronic earplug assembly of claim 33, wherein the outer housing is constructed from a material selected from the group consisting of polyvinylchloride, acrylic, a combination of polyvinylchloride and foam, and a combination of acrylic and foam.

37. The electronic earplug assembly of claim 33, wherein the transducer is attachment to the inner wall of the earplug outer housing.

38. The electronic earplug assembly of claim 33, wherein the transducer is attached to the distal end of a tube connecting the output of the acoustic driver.

39. The electronic earplug assembly of claim 33, wherein the controller comprises a feedback device.

40. The electronic earplug assembly of claim 33, wherein the controller comprises a feed forward device.

41. A method for designing an electronic earplug to provide active control attenuation of an acoustic signal at the tympanic membrane at frequencies greater than or equal to 1500 Hz, wherein the electronic earplug comprises an outer housing that extends into an ear canal to approximately the second bend and accommodates an acoustic driver and a transducer for measuring acoustic sound, and wherein the acoustic driver is located between a concha and the transducer and the transducer is located in an ear canal, and a controller, wherein the controller is connected to the transducer and the acoustic driver, the method comprising     generating a control signal at the controller in response to an acoustic signal originating external to the outer housing;

audibly broadcasting the control signal from the acoustic driver; and     locating the transducer in the outer housing to provide active control attenuation of an acoustic signal at the tympanic membrane at frequencies greater than or equal top 1500 Hz.

42. The method for designing an electronic earplug as in claim 41, wherein the acoustic driver is selected from the group consisting of a dynamic voice coil speaker a balanced armature receiver, and a piezoceramic device.

43. The method for designing an electronic earplug as in claim 41, wherein the transducer is selected from the group consisting of an electret microphone, a piezoelectric microphone, and a micro-machined silicon-band microphone.

44. The method for designing an electronic earplug as in claim 41, wherein the controller comprises a feedback device.

45. The method for designing an electronic earplug as in claim 41, wherein the controller comprises a feedforward device.

46. A method for designing an electronic earplug, wherein the electronic earplug comprises an outer housing that extends into an ear canal to approximately the second bend and accommodates an acoustic driver and a transducer for measuring acoustic sound, and wherein the acoustic driver is located between a concha and the transducer and the transducer is located in an ear canal, the method comprising:

determining a first complex sound pressure at the tympanic membrane;

determining a second complex sound pressure at the transducer; and     locating the transducer within the outer housing until the first complex sound pressure and the second complex sound pressure are substantially equal at frequencies up to 5 KHz.

47. The method for designing an electronic earplug as in claim 46, wherein the acoustic driver is selected from the group consisting of a dynamic voice coil speaker, a balanced armature receiver, and a piezoceramic device.

48. The method for designing au electronic earplug as in claim 46, wherein the transducer is selected from the group consisting of an electret microphone, a piezoelectric microphone, and a micro-machined silicon based microphone.

49. The method for designing an electronic earplug as in claim 46, wherein the first complex sound pressure at the tympanic membrane is determined using a probe situated to monitor the second complex sound pressure at a location in the ear canal away from the tympanic membrane, and wherein the first complex sound pressure is related to the second complex sound pressure by a transfer function determined using a means for emulating an ear canal and a tympanic membrane.

50. The method for designing an electronic earplug as in claim 49, wherein the means for emulating an ear canal and a tympanic membrane is selected from the group consisting of a one-dimensional transmission line acoustic model of the ear canal and tympanic membrane, a two-dimensional acoustic model of the ear canal and tympanic membrane, a three-dimensional acoustic model of the ear canal and tympanic membrane, a boundary element model of the ear canal and tympanic membrane, a finite element model of the ear canal and tympanic membrane, and an electrical analogue model of the ear canal and tympanic membrane.

51. The method for designing an electronic earplug as in claim 46, wherein the first complex sound pressure at the tympanic membrane is determined using a probe situated to monitor the pressure adjacent to the surface of means for emulating an ear canal and a tympanic membrane.

52. The method for designing an electronic earplug as in claim 51, wherein the means for emulating an ear canal and a tympanic membrane is selected from the group consisting of a one-dimensional transmission line acoustic model of the ear canal and tympanic membrane, a two-dimensional acoustic model of the ear canal and tympanic membrane, a three-dimensional acoustic model of the ear canal and tympanic membrane, a boundary element model of the ear canal and tympanic membrane, a finite element model of the ear canal and tympanic membrane, and an electrical analogue model of the ear canal and tympanic membrane.

53. An electronic earplug assembly comprising an outer housing, an acoustic driver for creating acoustic sound, and a transducer for measuring acoustic sound, and wherein the outer housing is adapted to:

decouple an acoustic path between an acoustic signal external to the outer housing and the tympanic membrane;

extend inside the ear canal to a sufficient depth to position the transducer along the ear canal so that a AM complex transfer function between the acoustic driver and the transducer is related to a second complex transfer function between the acoustic driver and the tympanic membrane such that a first sound pressure measured at the tympanic membrane and a second sound pressure measured at the transducer are substantially equal at frequencies up to 5 KHz.

54. The electronic earplug assembly of claim 53, wherein the outer housing is at least in part custom-molded.

55. The electronic earplug assembly of claim 53, wherein the outer housing comprises a combination custom-molded earplug base connected to a generic foam tip portion.

56. The electronic earplug assembly of claim 53, wherein the outer housing is constructed from a material selected from the group consisting of polyvinylchloride, acrylic, a combination of polyvinylchloride and foam, and a combination of acrylic and foam.

57. The electronic earplug assembly of claim 53, wherein the transducer is attached to the inner wall of the earplug outer housing.

58. The electronic earplug assembly of claim 53, wherein the transducer is attached to the distal end of a tube connecting the output of the acoustic driver.

59. The electronic earplug assembly of claim 53, wherein the transducer and acoustic driver are situated in a frame attached to the inner wall of the earplug outer housing.

60. The electronic earplug assembly of claim 53, wherein the transducer and acoustic driver are situated in a frame placed inside the earplug outer housing.

\* \* \* \* \*

UNITED STATES PATENT AND TRADEMARK OFFICE
CERTIFICATE OF CORRECTION

PATENT NO. : 7,024,010 B2
APPLICATION NO. : 10/440619
DATED : April 4, 2006
INVENTOR(S) : William R. Saunders et al.

It is certified that error appears in the above-identified patent and that said Letters Patent is hereby corrected as shown below:

Column 13:

Line 44, replace "wands" with --extends--
Line 47, replace "conchs" with --concha--
Line 67, replace "tympanic, membrane" with -- tympanic membrane--

Column 15:

Line 1, replace "Gsp" with -- $G_{sp}$ --
Line 5, replace "Gc" with -- $G_c$ --
Line 10, replace "Gp,e" with -- $G_{p,e}$ --
Line 14, replace "Gp,tm" with -- $G_{p,tm}$ --
Line 16, before "determining", insert a line break
Line 17, replace "Pd,e" with -- $P_{d,e}$ --
Line 20, replace "Pd,tm" with -- $P_{d,tm}$ --
Line 23, after "defined by" insert -- – --
Line 24, replace "Pt,e" with -- $P_{t,e}$ --
Line 25, replace "Pd,e" with -- $P_{d,e}$ --
Line 30, after "by" insert -- $$\frac{P_{t,tm}}{P_{d,tm}} = 1 - \frac{G_{p,tm} G_c G_{sp}}{1 - G_c G_{sp} G_{p,e}}$$ --

Line 30, replace "Pt,tm" with -- $P_{t,tm}$ --
Line 31, replace "Pd,tm" with -- $P_{d,tm}$ --
Line 37, replace "Fix" with -- $P_{t,tm}$ --

Column 16:

Line 37, replace "cloned" with -- cloned--

Column 17:

Line 17, replace "top" with --to--

UNITED STATES PATENT AND TRADEMARK OFFICE
CERTIFICATE OF CORRECTION

PATENT NO. : 7,024,010 B2
APPLICATION NO. : 10/440619
DATED : April 4, 2006
INVENTOR(S) : William R. Saunders et al.

It is certified that error appears in the above-identified patent and that said Letters Patent is hereby corrected as shown below:

<u>Column 18</u>

Line 34, replace "AM complex" with --complex--

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,024,010 B2 | Page 1 of 1 |
| APPLICATION NO. | : 10/440619 | |
| DATED | : April 4, 2006 | |
| INVENTOR(S) | : William R. Saunders et al. | |

It is certified that error appears in the above-identified patent and that said Letters Patent is hereby corrected as shown below:

Column 1, line 5, insert the following section title and paragraph, before the section entitled "Field of Invention":

--GOVERNMENT RIGHTS

This invention was made with Government support under contract F33615-02-C-6021 awarded by the Department of the Air Force. The Government has certain rights in this invention. The U.S. Government has a paid-up license in this invention and the right in limited circumstances to require the patent owner to license others on reasonable terms as provided by the terms of contract F33615-02-C-6021 awarded by the Department of the Air Force.--

Signed and Sealed this

Twenty-second Day of December, 2009

David J. Kappos
*Director of the United States Patent and Trademark Office*